United States Patent [19]

Van Arnam et al.

[11] 4,368,982
[45] Jan. 18, 1983

[54] RETROREFLECTOMETER

[75] Inventors: Donald E. Van Arnam, Ontario; Earl W. McFeaters, La Crescenta; Richard R. Baggarley, Arcadia, all of Calif.

[73] Assignee: Avery International Corporation, San Marino, Calif.

[21] Appl. No.: 157,791

[22] Filed: Jun. 9, 1980

[51] Int. Cl.³ ............................................. G01N 21/01
[52] U.S. Cl. ...................................... 356/445; 250/224
[58] Field of Search ................................. 356/445–448; 250/224, 234

[56] References Cited

U.S. PATENT DOCUMENTS 3,214,596 10/1965 Schwerdt, Jr., et al. .
3,229,564 1/1966 Meltzer .
3,782,827 1/1974 Nisenson et al. ............... 356/447 X
4,097,751 6/1978 Egan et al. ...................... 356/447 X
4,125,328 11/1978 Suga .
4,201,474 5/1980 Holl et al. ........................ 356/445 X

FOREIGN PATENT DOCUMENTS 2905727 11/1979 Fed. Rep. of Germany ...... 356/448

Primary Examiner—Bruce Y. Arnold
Attorney, Agent, or Firm—Christie, Parker & Hale

[57] ABSTRACT

Apparatus and methods for measuring retroreflective properties of a surface are disclosed. The apparatus and methods are characterized in that the measured angle of divergence is varied while the angle of incidence is simultaneously varied.

15 Claims, 6 Drawing Figures

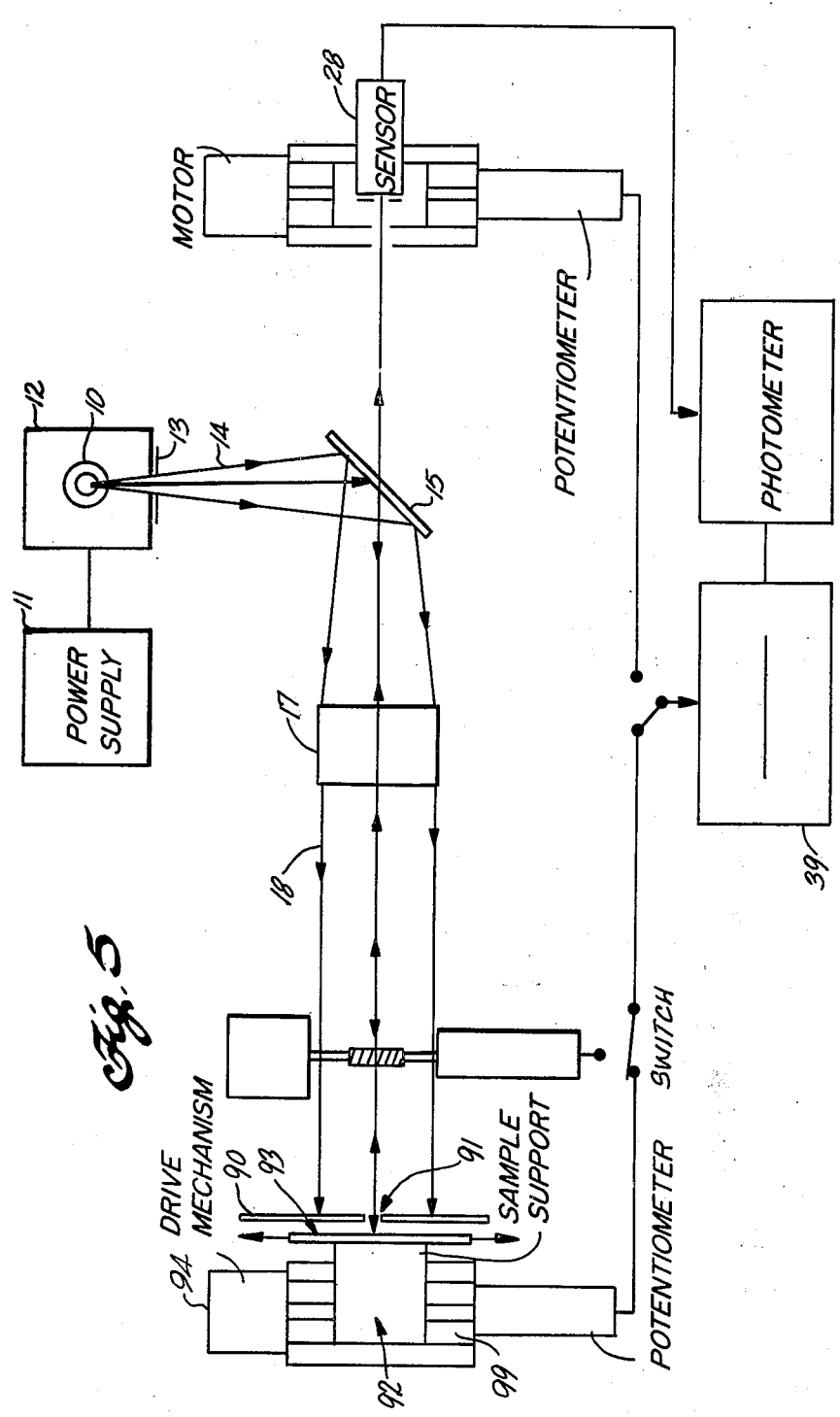

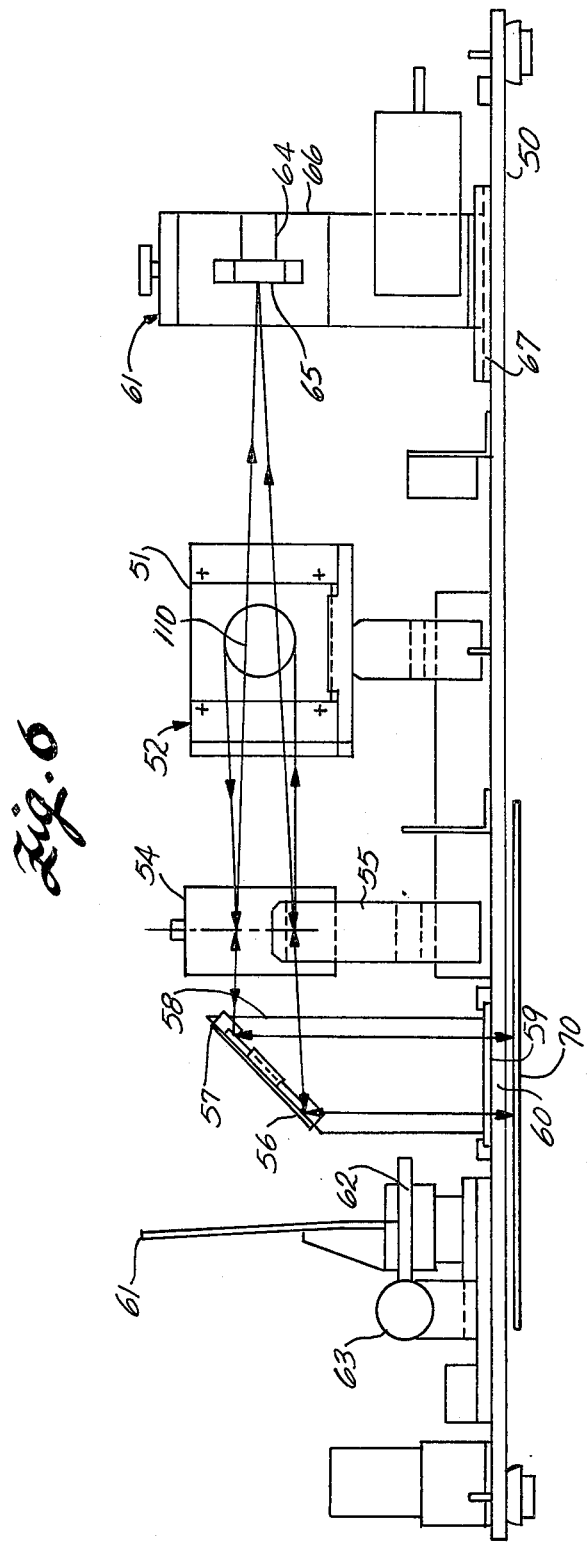

RETROREFLECTOMETER

BACKGROUND OF THE INVENTION

The present invention relates to apparatus and methods using such apparatus for measuring retroreflective properties of a surface. In particular, the apparatus can be useful in measuring the brightness at angles of divergence of light retroreflected from a surface and also the effect on retroreflective properties when the angle of incidence changes.

Retroreflective surfaces offer reflective capabilities not available with diffuse or mirrored surfaces with regard to reflecting incident light back toward the light source. For example, mirrored surfaces are able to reflect light back to the light source only when the light source is at a 90° angle to the mirrored surfaces. Therefore, if an observer is at the light source, the mirrored surface would only appear bright when the observer is at such a 90° angle to the surface.

Retroreflective surfaces have found increasing use because of their ability to reflect incident light back towards the light source. For example, retroreflective surfaces are used in constructing signs for use along roads and highways and in making easily observed "reflectors" for use on objects such as vehicles, posts, mailboxes and the like.

Currently some retroreflective surfaces are constructed by carefully arranging in a composite structure various individual optical elements. Retroreflective surfaces are also constructed by forming a surface of spherical beads over a reflective surface, such as an aluminized reflective surface. For such a retroreflective surface the incident rays are focused by the beads at about the beads' back surfaces or beyond. The light is reflected by the mirrored surface, back through the beads and refracted at the beads' front surfaces which direct the light generally back to the source.

Another type of retroreflective surface utilizes prismatic reflectors such as cube corner prisms disposed along a surface. In such prismatic reflectors the incident light is refracted upon entering the prism, thrice reflected by the back surfaces of the prism and refracted upon exiting the prism to return the light generally to its source.

It is desirable to define two terms used herein. The term "incidence angle" is the angle formed by the incident light rays to a line perpendicular to a reflective surface. The term "divergence angle" is the angle between a line formed by the source light ray (incident light ray) and the retroreflected light ray back to the observer.

The currently accepted method for measuring retroreflectivity is described in pages 11-12 and 18 of Federal Specification L-S-300C. The apparatus described therein consists of a projector, means for mounting the retroreflective sheeting and a detector that is precisely positioned near the projector. The projector has a maximum lens diameter of one inch and is capable of projecting a uniform light. The light reflected from the test surface is measured with a photoelectric receiver. The photoelectric receiver has dimensions such that no point on the perimeter is more than one-half inch from the center. The samples are mounted on a flat black test surface not less than three feet square. The sample is placed 50 feet plus or minus 2 inches from the projector lens and the receiver. To conduct the reflectivity test the angles of incidence and divergence are set and the reflectivity determined by the following equation:

$$R = \frac{Er \, (d)^2}{Es \, (A)}$$

wherein R is the reflective intensity, Er is the illumination incident upon the receiver, Es is the illumination incident upon a plane perpendicular to the incidence ray at the specimen position, d is the distance from the specimen to the projector, and A is the area of the test surface. Drawbacks of this method are that it measures the reflective properties at set angles and requires a long room in which to conduct the test.

Other instruments have been devised to facilitate measuring retroreflective properties other than using the government recommended procedure above. Such other methods avoid the necessary long, dark room (50 feet at least) needed to conduct the above test. U.S. Pat. No. 3,214,596 to Schwerdt, Jr. et al describes apparatus for detecting retroreflected light. The apparatus detects retroreflected light but does not have the capacity to measure the effect on retroreflectivity by changing the angle of incidence and divergence.

U.S. Pat. No. 3,229,564 to Metzer describes apparatus for measuring reflected light and especially specularly and diffusely reflected light. Because of the apparatus' ability to measure specularly reflected light, the apparatus would also be capable of measuring retroreflected light when the incident light is perpendicular to the mirrored surface.

U.S. Pat. No. 4,125,328 to Suga relates to apparatus for measuring reflectivity or transmissivity of a surface. In the apparatus means are provided for changing the angle of incidence and the angle of reflectance through which the intensity of the reflected light is measured. No means is provided for measuring retroreflected light or retroreflective properties of the surface.

A method and apparatus is desirable in the art which could provide direct measurement of the effects on retroreflective properties of changing the angle of incidence and angle of observation (divergence angle) of light incident to and reflected by a retroreflective surface. Apparatus which could provide a continual monitoring of retroreflective properties while such angles were changing would also be desirable in the art. Such apparatus would be especially desirable if it were compact (i.e., much less than 50 feet in length), easy to use, precise and accurate in measuring the retroreflective properties.

SUMMARY OF THE INVENTION

The present invention relates to apparatus and methods for measuring retroreflective properties of a surface. The apparatus can be used to obtain a complete characterization of a retroreflective surface. The retroreflected light intensity can be measured as a function of divergence angle at fixed incidence angles or as a function of incidence angularity characteristics at fixed divergence points. The apparatus also permits recording retroreflected light as a function of simultaneously changing both the divergence and incidence angles at varying rates, such as to simulate what is observed by one approaching an illuminated retroreflective sign at night in a moving vehicle.

The apparatus described herein is referred to as a retroreflectometer because of its ability to measure heretofore generally unmeasurable characteristics of retroreflected light and retroreflective surfaces. In particular, the retroreflectometer provides an apparatus useful for determining loss of retroreflective intensity at specific or varying divergence angles.

The apparatus comprises a light source. The light source provides a point source of light such as can be provided by placing an apertured surface in front of the light source. The point light source provides a light beam which is directed to a beamsplitter. The beamsplitter is positioned to reflect the light beam from the light source toward a collimating lens. The light passes through the lens and is collimated. A target for holding the retroreflective sample being evaluated is positioned to intercept the collimated light. The target is adapted to support the sample in the collimated light and to rotate the sample for changing the angle of incidence of the collimated light striking the sample. An element is provided for determining the position of the target (or sample) with regard to the collimated light.

The light is retroreflected by the retroreflective surface of the sample back through the collimating lens toward the beamsplitter. As the retroreflected light passes back through the collimating lens it is focused, i.e., converged to a focal point. The retroreflected light passes through the beamsplitter toward a detector, such as a photodiode sensor, positioned at or near the focal point of the collimating lens. The detector is positionable along X and Y axes (in a plane perpendicular to the light path) to detect the intensity of the retroreflected light and how it diverges with each sample.

The detector can be connected to various display instruments to provide a readout or visual display of the measured intensity. Such display instruments can include X-Y recorders, digital readout instruments, memory storage units and the like.

The apparatus can be enclosed in a housing and supported on a base within the housing. The housing is essentially a black box which effectively prevents outside light from entering.

The apparatus can also include a sample support capable of supporting a sample to be evaluated and moving the sample for traversing the collimated light. A slotted surface having a narrow slot extending thereacross is positioned for intercepting the collimated light and passing a narrow beam of the collimated light for illuminating the sample along narrow bands as it traverses the narrow beam of collimated light. A narrow band on the surface of the sample is illuminated which provides for evaluation of the retroreflective properties of the sample in such narrow bands. By traversing the sample through the narrow beam of collimated light the entire surface can be evaluated. A position indicator can monitor the position of the sample being evaluated.

The apparatus can also include a mirror positioned between the collimating lens and target. The mirror can reflect the collimated light downwardly, below the retroreflectometer onto a sample too large to be held on the target. The housing for the retroreflectometer can have an opening for permitting the light to exit the housing below the mirror. The light is retroreflected by the surface of the sample and directed back to the mirror. The light is reflected by the mirror through the lens and beamsplitter to the detector.

BRIEF DESCRIPTION OF THE DRAWINGS

These and other features and advantages of the present invention will be appreciated as the same becomes better understood by reference to the following detailed description of presently preferred embodiments when considered in connection with the accompanying drawings wherein:

FIG. 5 is a schematic top view of another embodiment of apparatus herein;

FIG. 6 is a schematic side view of another embodiment of apparatus herein for measuring retroreflective properties of large retroreflective surfaces.

DETAILED DESCRIPTION OF THE INVENTION

The apparatus for measuring retroreflective properties of a surface and the method for measuring such retroreflective properties using the apparatus is herein described with regard to the accompanying drawings.

Figure 1:
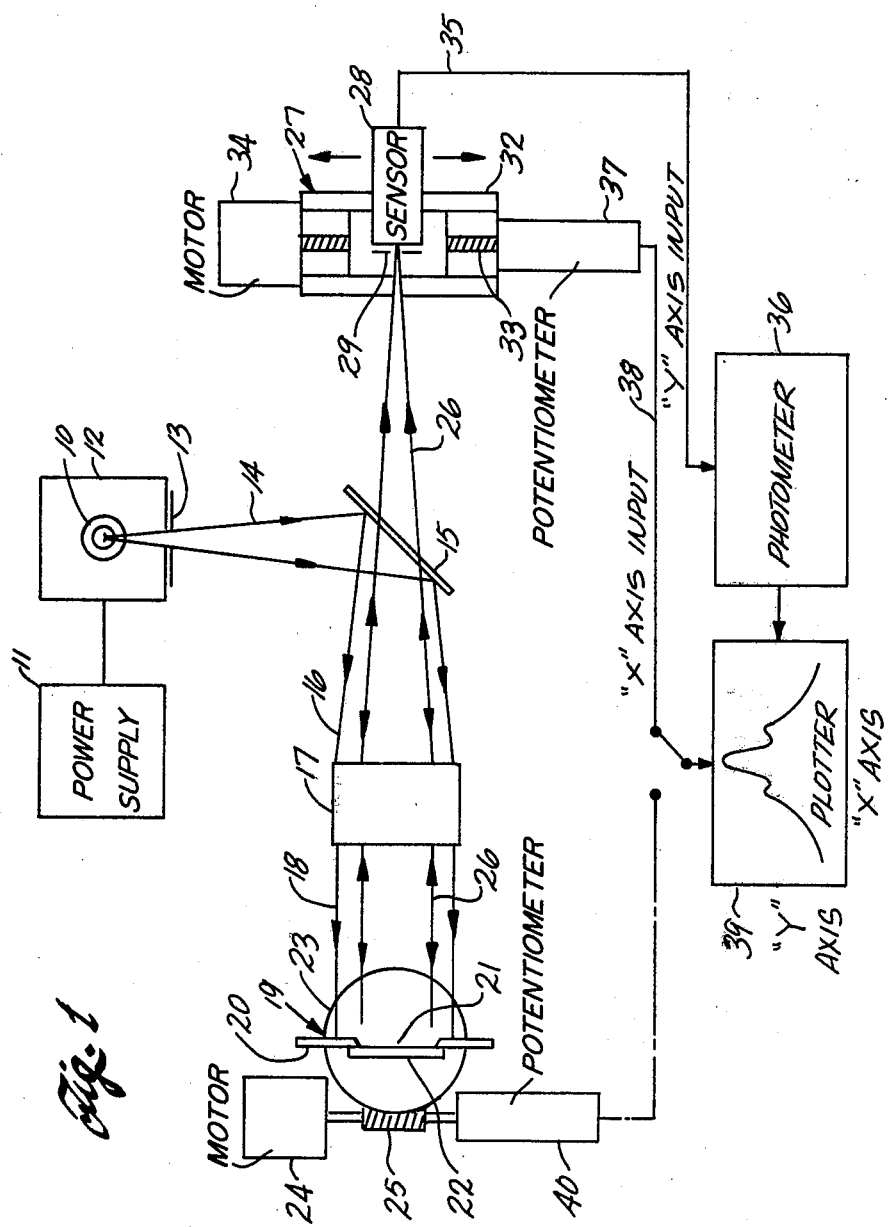
FIG. 1 is a schematic top view of apparatus for measuring retroreflective properties of a surface and illustrating the use of the apparatus to measure the divergence brightness profile of light reflected from a retroreflective surface.

With reference to FIG. 1, an embodiment of the apparatus is schematically illustrated. Although not shown in the drawings, it is preferred that the elements of the apparatus be enclosed within a housing. The housing can comprise a container-like configuration, such as a rectangular box, for housing the apparatus. Preferably, the housing is constructed to essentially make the housing a black box. That is, the housing is so constructed as to prevent outside light from entering. It is undesirable to have outside light enter the housing during the course of a measurement of retroreflective properties as such outside light can effect and lead to erroneous light measurements. The housing can also be provided with the necessary utility lines, such as power supply lines for feeding power to the components of the apparatus requiring power and can be provided with appropriate connectors for carrying signals from the apparatus.

The housing can be provided with the necessary supports for supporting the various elements of the apparatus within the housing. For example, the housing can be provided with a base 50 (not shown in FIG. 1 but shown in FIG. 6) on which the various elements can be supported. The base can provide the surface for maintaining the proper attitude, spacing and configuration of the various components.

With regard to FIG. 1, the apparatus comprises a light 10 which is the source illuminating source for the retroreflective surface to be evaluated. The light source can be any light source, such as an arc lamp, laser, incandescent lamp, and the like. Specifically, the light source can be a zirconium or a tungsten light source at a color temperature at or near 2854° K. (equivalent to CIE Std. Source A). The power of the light source 10 can vary. Sufficient brightness is needed to illuminate the surface to be evaluated and be retroreflected thereby to provide retroreflected light of sufficient intensity to be detectable. A power supply 11 can be provided for supplying power to the light source 10. The power supply can be either external or within the housing.

The light emitted by the light source can be controlled and made directional by an apertured surface 13. Such an apertured surface can be part of the light source housing 12, can be placed within the light housing or be located outside of the light housing. The apertured surface 13 is a surface having an aperture therein for permitting the light from the light source to pass therethrough. The aperture is positioned to pass the light to a beamsplitter 15. The apertured surface 13 can be a surface in which the aperture can be enlarged or made smaller depending upon the power of the light source. The opening of the aperture is controlled to flood the surface of the sample being evaluated with light. If the aperture is too large, unnecessary light can be reflected within the apparatus. If the aperture is too small then the total surface is not evaluated. If the light source 10 is a laser, the apertured surface can be omitted. However, the apertured surface can be retained if it is desired to decrease the dimensions of the light emitted by the laser.

A light beam 14 is emitted by the light source 10 and is directed through the aperture to a beamsplitter 15. The beamsplitter 15 can be a piece of glass, front partially metalized mirror, prism, pellicle and the like. The beamsplitter partially reflects light striking its surface. The light beam 14 strikes the beamsplitter and is reflected at about a right angle. The reflected light 16, reflected from the beamsplitter, passes through a collimating lens 17. The collimating lens collimates light passing through it in one direction and focuses light passing through the lens in the opposite direction converging such light to a focal point. The reflected light 16 forms a collimated light beam 18. The collimating lens 17 can be supported by a support (not shown) which permits the collimating lens to be moved either toward or away from the beamsplitter. The ability to move the collimating lens is desirable as the lens can be moved to capture all of the reflected light 16 reflected from the beamsplitter and to focus the light passing back through the collimating lens. The light rays in the collimated light beam 18 are essentially parallel.

The collimated light beam 18 is directed to a target 19. The target comprises a sample holder 20 having an opening 21 which exposes a sample 22 to the collimated light. The sample 22 comprises a reflective or retroreflective surface for which the retroreflective characteristics are to be evaluated. For example, the sample can be a cube-corner prismatic retroreflective sheeting. The sample holder 20 supports the sample within the beam of collimated light. The sample holder also supports the sample such that the plane of the sample surface is vertically oriented relative to the essentially horizontal collimated light beam. The opening 21 in the sample holder can be varied to enlarge or decrease the size of the opening.

The target 19 also comprises a rotary table 23. The rotary table 23 supports the sample holder 20. The rotary table can be rotated to change the angle of incidence of the collimated light beam 18 as it strikes the sample in the sample holder. The rotary table can be rotated 360° but, in effect, need only be rotated through 180° to present a variety of angles or incidence to the collimated light striking the sample. The rotary table can be rotated by any suitable drive mechanism such as a motor 24 which powers a worm gear 25.

The retroreflected light 26 from the sample of retroreflective material is passed through the collimating lens 17. As the retroreflected light 26 passes through the collimating lens, it is focused and travels in a converging pathway. The retroreflected light, after passing through the collimating lens, passes through the beamsplitter 15. The retroreflected light 26 that passes through the beamsplitter is focused on a detector 27. The detector 27 comprises a light sensor 28. The light sensor 28 can be a vacuum photodiode sensor, photomultiplier, diode, and the like for sensing the intensity of the light striking it. The retroreflected light 26 is focused at the sensor plane by the collimating lens 17. The sensor 28 detects the light flux striking it and converts such detected light flux to an electric signal.

The detector 27 can comprise an apertured surface 29, such as a black, nonreflective surface having a variable diameter opening therein. The opening in the apertured surface can be quite small, such as about the diameter of a pinhole. The lower limit with regard to size of the aperture is preferably as small as possible and limited by diffraction of the light and sensitivity of the light sensor. The diameter of the aperture can be varied to increase or decrease the amount of light that passes therethrough. In a working embodiment of apparatus as described in FIG. 1, the apparatus had a sample to sensor distance of approximately 30 inches, the opening of the aperture was about 0.02 inch.

In a working model of the apparatus described in FIG. 1, the sensor comprised a vacuum photodiode with a photopic filter. Such a sensor and filter combination was selected to match the sensitivity of the human eye. Sensors with alternate filters, such as one to match radiometric characteristics, could replace the photopic filter.

The detector 27 also comprises a drive mechanism including a drive motor 34, for providing both X and Y movement to the sensor. The sensor can be moved along the Y-axis (vertically) by appropriate gearing (not shown) to position the sensor for receiving the optimum intensity of the retroreflected light. In addition, the sensor can be moved vertically to detect the intensity of the retroreflected light from the sample as a function of vertical movement.

A horizontal drive mechanism 32 for moving the sensor along the X-axis (horizontally) can be any suitable drive mechanism. For example, the drive mechanism 32 is shown in the figure as comprising a worm gear 33 which permits the sensor to be moved horizontally. As the sensor can be moved horizontally, it can be used to detect the intensity of the light as a function of such horizontal movement. That is, the sensor can be moved to detect the divergence properties of the retroreflective surface.

The sensor is moved vertically and/or horizontally by a motor 34 which can activate either the horizontal (X-axis) or vertical (Y-axis) drive mechanism for the sensor or can activate both such mechanisms at the same time.

FIG. 1 also shows a utility of the apparatus in a mode of operation for determining the divergence of light retroreflected from a retroreflective surface. The mode of operation illustrated in FIG. 1 provides for determining the intensity of retroreflected light as a function of the divergence angle for a given angle of incidence.

The method is performed by inserting the sample of the retroreflective surface to be evaluated in the sample holder 20. The plane of the sample is then adjusted to provide the desired incidence angle. As illustrated in FIG. 1, a 0° incidence angle has been selected. This angle can be adjusted because the sample holder is supported on the rotary table 23. The power supply is engaged to activate the light source 10. The light from the light source passes through the aperture and strikes the beamsplitter 15. The light is reflected toward and through the collimating lens 17. The collimated light strikes the retroreflective surface in the sample holder. The retroreflected light rays are retroreflected through the collimating lens and focused in a converging pattern through the beamsplitter onto the sensor 28. The height of the sensor is adjusted to intercept the retroreflected light 26 with regard to vertical at the height which provides the greatest intensity of retroreflected light (i.e., optical center).

When the sensor has been adjusted to such a height, the sensor is moved horizontally. The sensor is moved away from the optical center and, therefore, away from the focused retroreflected light 26. The motor 34 is activated to drive the sensor horizontally across the retroreflected light through the optical center for scanning across the beam of retroreflected light at the preset height.

The position of the sensor is monitored by a potentiometer 37. The potentiometer provides a signal which can be plotted along an X-axis of a suitable plotter 39. The sensor detects the intensity of the retroreflected light and transforms the intensity to an electric signal such as through a photometer 36. The output signal from the photometer 36 can be fed to the plotter 39 as the Y-coordinate. In operation, the sensor traverses the retroreflected light pattern at the predetermined height, senses the intensity which is amplified by the photometer and records the intensity. The X-axis position corresponding to the sensed intensity is monitored by the potentiometer and also recorded. The plotter 39 shows a typical curve formed wherein the intensity of retroreflected light is a function of the divergence angle.

Figure 3:
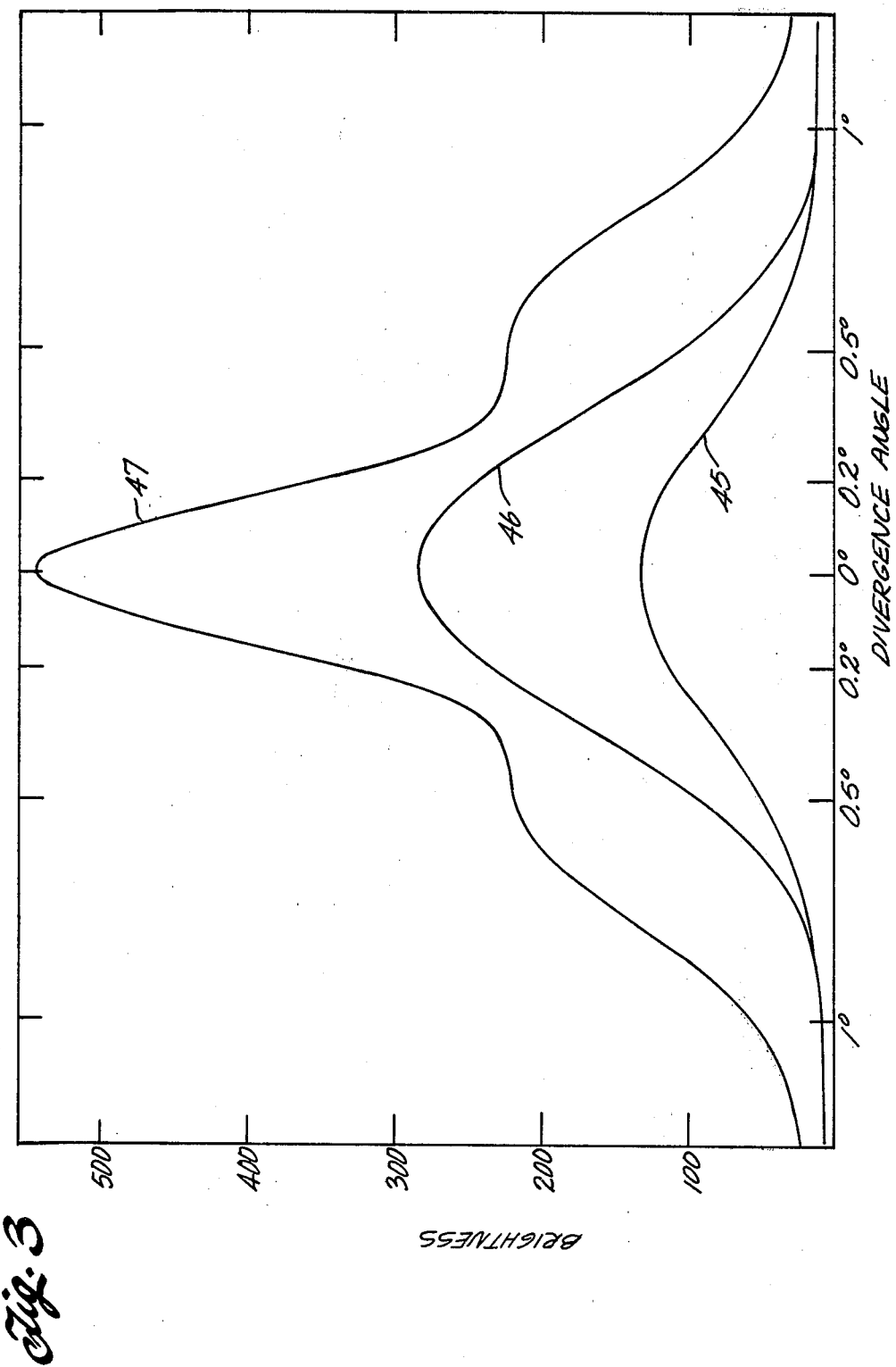
FIG. 3 is a diagram illustrating the effect on intensity of retroreflected light as a function of the divergence angle.

FIG. 3 is a diagram of three typical curves produced by the above-described method for measuring the intensity of retroreflected light as a function of the divergence angle. The curve designated 45 is a typical curve for an engineer grade (enclosed lens) retroreflective surface. As is apparent from the drawing, there is some divergence of the retroreflected light from such a surface.

The curve 46 is a typical curve for an encapsulating lens type retroreflective surface, 3M high intensity retroreflective sheeting commercially available from 3M Company. This curve shows that the encapsulated lens type retroreflective surface is brighter than an engineer grade retroreflective surface.

The curve 47 is a curve formed using a cube-corner prismatic retroreflective surface. The curve shows that the cube-corner prismatic surface provides intense retroreflectivity out to high divergence angles.

Figure 2:
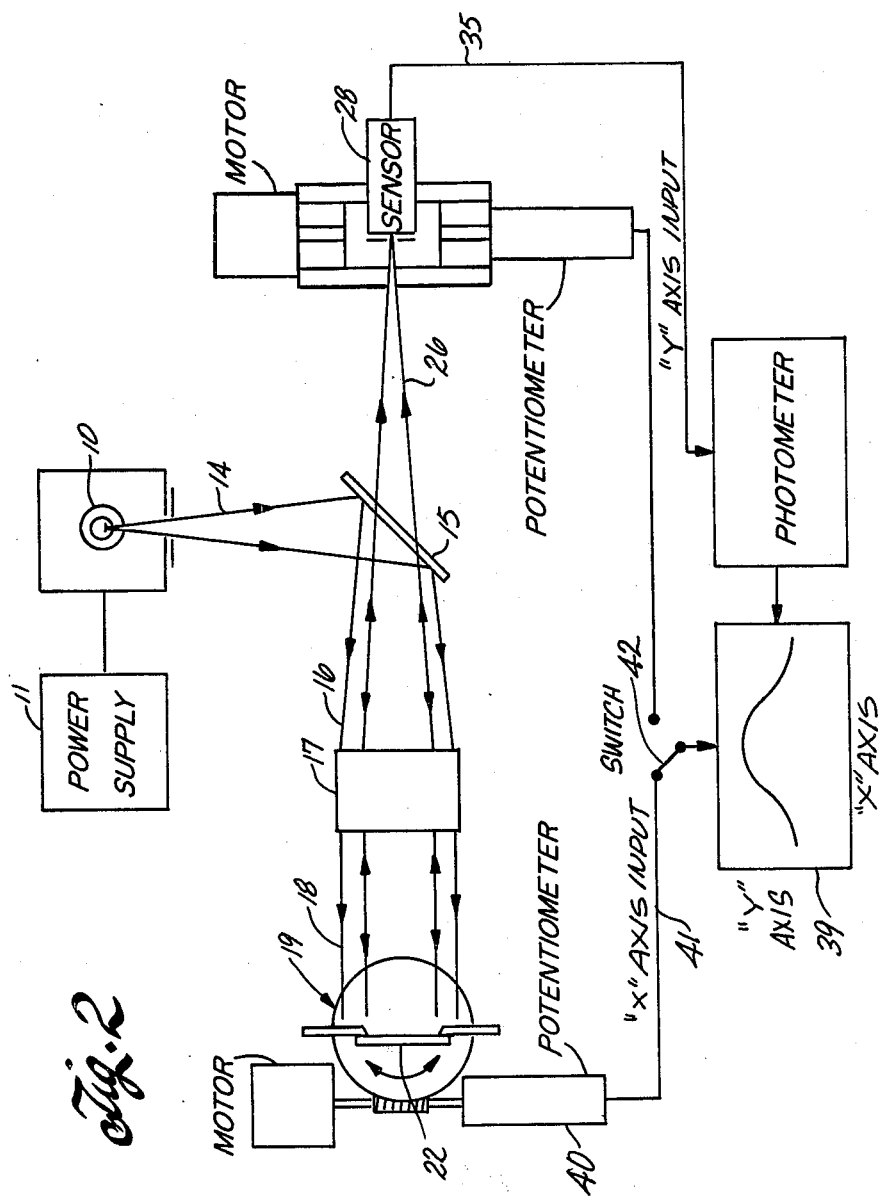
FIG. 2 is a schematic view of the apparatus of FIG. 1 illustrating the use of the apparatus to measure the effect on retroreflectivity by changing the angle of incident light.

The apparatus described in FIG. 1 is also illustrated in FIG. 2. The apparatus shown in FIG. 2 is identical to the apparatus of FIG. 1 except the apparatus is shown being utilized in a method for determining the intensity of retroreflected light as a function of the angle of incidence on the retroreflective surface. That is, FIG. 2 depicts the retroreflectometer apparatus in an alternate mode for recording incidence angle characteristics at a fixed divergence point.

In FIG. 2 the retroreflective material to be evaluated is placed in the sample holder. The sensor 28 is positioned at the desired divergence angle to be evaluated. The light source is activated and the light strikes the beamsplitter, is reflected through the collimating lens and onto the sample. The sample is rotated. The rotary table 23 rotates and its position is monitored by a potentiometer 40. The potentiometer sends a signal 41 as the input to the X-axis of a suitable readout instrument such as a plotter 39.

The light retroreflected from the surface of the sample passes through the collimating lens and is focused on the sensor. The sensor detects the intensity of the retroreflected light and sends a signal to the photometer 36. The intensity is recorded on the Y-axis of the readout instrument. A typical curve for retroreflective material is illustrated on the plotter 39 in the drawing.

Figure 4:
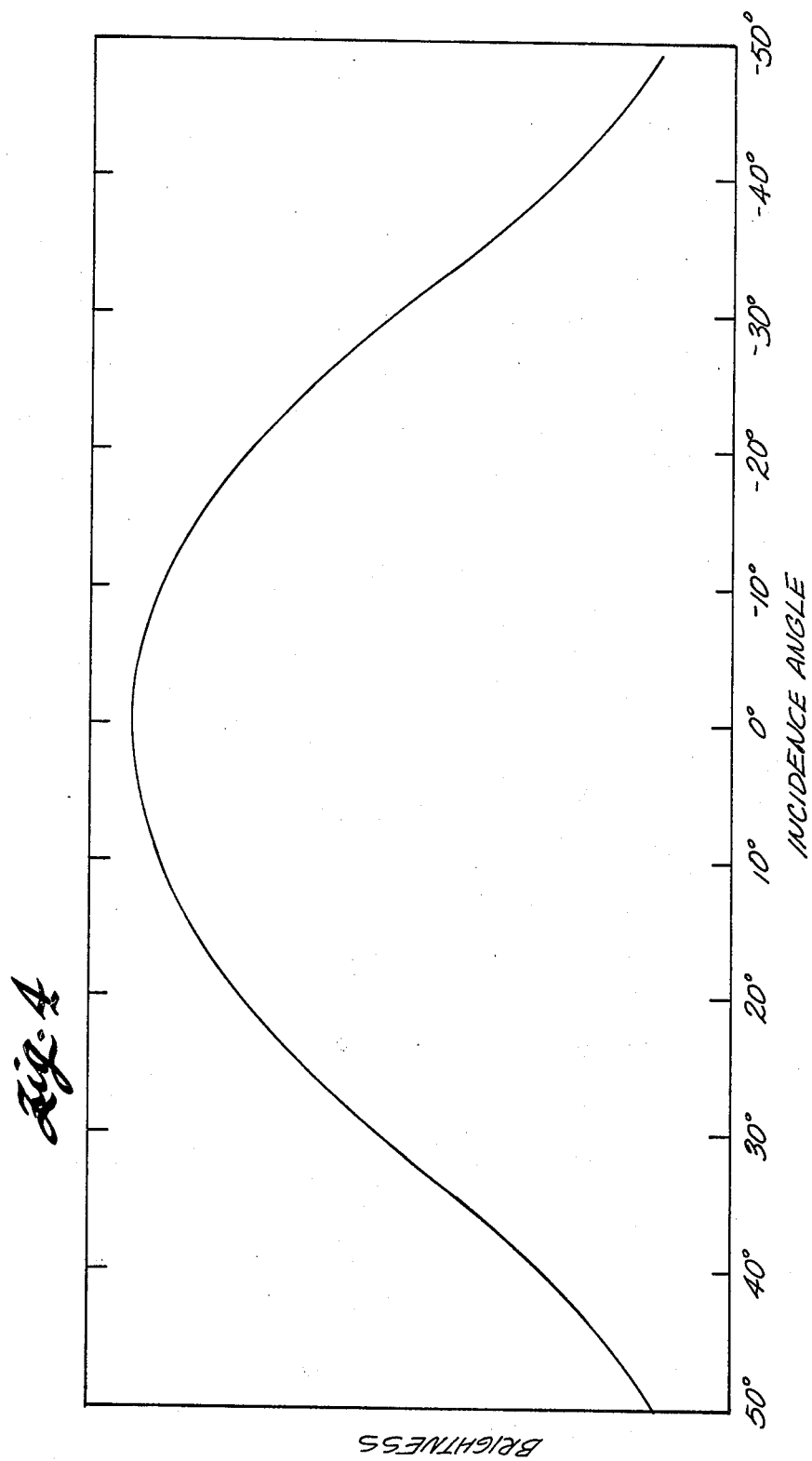
FIG. 4 is a diagram illustrating the effect of changing angle of incidence on the intensity of retroreflected light.

FIG. 4 is an illustration of a typical curve of retroreflective brightness at a fixed divergence angle but varying incidence angles.

The retroreflectometer herein also provides the ability to measure the intensity of retroreflected light as a function of both the angle of incidence and divergence. That is, the intensity of the retroreflected light can be measured while changing the angle of incidence and simultaneously changing the angle of divergence. Such a test is valuable as it can duplicate what occurs when an automobile is advancing toward a road sign. As the automobile approaches the road sign the angle of the light striking the road sign (incidence angle) increases. The angle of divergence also increases.

An embodiment of the retroreflectometer for use in measuring the retroreflective characteristics of discrete areas of a retroreflective surface being evaluated is illustrated in FIG. 5. For ease of description, the elements of the embodiment illustrated in FIG. 5 that are equivalent to like elements shown in FIGS. 1 and 2, are shown using the same reference numerals.

With regard to FIG. 5, the apparatus therein is essentially the same as the apparatus of FIGS. 1 and 2. However, the target 19 of FIGS. 1 and 2 has been removed to permit the collimated light 18 to continue past the location of the target 19. The rotary table and drive mechanism can be left in place as it does not interfere with the collimated light. For example, the collimated light can pass above such elements.

In addition to the above described and illustrated elements, the apparatus comprises a slotted surface 90. The slotted surface 90 has one slot 91 extending thereacross. The slot 91 can extend in any direction across the slotted surface 90. The slot is shown as extending vertically across the slotted suface. The slot can be other configurations other than a slot, i.e., circular, square, etc. The dimension and configuration controls the area illuminated on the sample surface. The dimensions for the slot are such as to avoid diffraction of the collimated light. Generally, a size less than 1 mm in width is undesirable because of diffraction but can be used. The slotted surface is preferably a non-reflecting surface. Such a non-reflecting surface can absorb the collimated light rays not passing through the slot and thus reduce the possibility of light reflecting from the slotted surface interfering with the measurements to be made.

A sample support 92 is spaced from the slotted surface such that the slotted surface intercepts the collimated light 18 before such light reaches the sample support. The sample support 92 supports a sample 93 of a retroreflective surface to be evaluated. The sample 93 is supported in a manner that can permit collimated light passing through the slot to strike and illuminate the retroreflective surface along a narrow band or strip.

The sample support has a drive mechanism 94 which can move the sample support in a direction of travel that is generally at right angle to the extending slot 91. That is, for a vertically extending slot, the sample support travels in a generally horizontal direction and correspondingly if the slot extends horizontally then the path of travel is vertical. The drive mechanism can be a motor and worm gear.

The embodiment illustrated in FIG. 5 can be used to evaluate a sample of a retroreflective surface in discrete areas of the surface. To perform such an evaluation, the light source 10 is activated and the light emitted is reflected by the beamsplitter 15, through the collimating lens 17 toward the slotted surface 90. The collimated light striking the slotted surface is absorbed by the slotted surface. A portion of the collimated light 18 passes through the slot 91 in the slotted surface. The collimated light passing through the slot illuminates the retroreflective sample along a narrow band or strip.

The light striking the retroreflective sample is retroreflected from its surface back through the slot and through the collimating lens. As the retroreflected light passes through the collimating lens, it is focused through the beamsplitter toward a sensor 28. The sensor is positioned to intercept the retroreflected and focused light at about its optical center. The sensor senses the intensity of the retroreflected light. The intensity of the retroreflected light can be amplified by a photometer and recorded as the Y-axis input to a suitable plotter 39.

As the light is passing through the slot, the drive mechanism is activated to move the sample support and sample of retroreflective surface across the portion of collimated light passing through the slot in the slotted surface. The movement of the sample support causes the sample to traverse across the portion of the collimated light such that the narrow beam of collimated light illuminates the retroreflective surface in discrete areas. The location or position of inpingement of the collimated light on the retroreflective sample surface can be monitored and with a suitable potentiometer fed as a signal to the plotter 39 as the X-axis input. If the retroreflective sample has uniform retroreflective properties across its surface, a straight line is generated as shown on the plotter. If variations occur in the retroreflective properties of the sample, then the line generated can be a jagged line showing the areas wherein the retroreflective properties are distorted.

This method of operation of the retroreflectometer apparatus permits the close scrutiny of a surface to observe its retroreflective properties. If aberrations along the surface do occur, their position can be noted for further review, such as for determining how such aberrations occurred.

The embodiment and mode of operation discussed above with regard to FIG. 5 can also be used in combination with the methods of operation disclosed with regard to FIGS. 1 and 2. That is, a slotted surface can be used in the methods that measure the intensity of retroreflected light as a function of the incidence angle or divergence angle. In such methods, the sample to be evaluated can be traversed across the narrow ray of collimated light beam at differing incidence or divergence angles.

Another embodiment of the retroreflectometer apparatus is illustrated in FIG. 6. The embodiment depicted in FIG. 6 provides for measuring the retroreflective properties of a large retroreflective surface, such as samples too large to be held in the sample holder 61.

FIG. 6 is a side view of the apparatus. The light source 110 is shown in phantom as it is hidden behind a beamsplitter 51. The beamsplitter 51 is supported on a support 52 which can be rotated for directing the light reflected from the beamsplitter 51. A collimating lens 54 is supported by a collimating lens support 55 attached to the base 50. The collimating lens is as described above with regard to FIGS. 1, 2 and 5.

The added elements of the embodiment in FIG. 6 comprise a mirror 56, mirror holder 57, mirror holder support 58, mirror support slide 59, and an opening 60 in the housing.

A fully reflecting front surfaced mirror 56 is interposed between the collimating lens 54 and the sample holder 61. The mirror is positioned to reflect the light rays from the collimating lens through a provided opening 60 in the housing. The opening 60 can be in any of the walls of the housing including the top, bottom or sidewalls. In use for measuring divergence characteristics of large samples the apparatus can be set against or upon a sample 70 to be evaluated. The rays of retroreflected light are retroreflected from the surface of the sample back to the mirror 56.

The front surfaced mirror 56 is supported in a mirror holder 57 which can be adjusted to provide an angularity to the mirror which reflects the light onto the surface of the sample. The mirror holder 57 is attached to a mirror support slide 58 which provides adjustment of the position of the mirror relative to the collimating lens 54.

The opening 60 in the base 50 can be an opening which can be opened or closed, and/or adjustable in size. For example, when the apparatus is being used to measure small samples in the sample holder 61, the opening is preferably closed to prevent light from entering the housing.

The retroreflected light from the sample is retroreflected back through the opening 60 to the front surfaced mirror 56. The light reflects from the mirror, back through the collimating lens 54 which focuses the retroreflected light through the beamsplitter 51 onto a detector 64 and more specifically the planar surface of a sensor 65. The detector 64 comprises the sensor 65 and drive mechanism 66 for vertical movement and support of the sensor and a drive mechanism 67 for horizontal movement of the sensor.

The sensor can be the same as described above with regard to FIGS. 1, 2, and 5. A motor (not shown) can be part of the drive mechanisms 66 and 67 for moving the sensor in either the vertical or horizontal direction.

In further regard to FIG. 6, a motor 63 is shown for activating the rotary table 62 for the sample holder 61. The side view presented in FIG. 6 shows the orientation of the elements described above with regard to FIGS. 1, 2 and 5.

The test method described in L-S-300C utilizes a relatively large sensing area, i.e., one inch diameter. This represents approximately 0.1° divergence at 50 feet. Slight errors in the divergence placement of the detector can, therefore, cause substantial measurement errors in the retroreflected light detected by the sensor.

In some cases the intensity of the retroreflected light drops sharply as a function of the divergence angle (see FIG. 3). Thus, a good retroreflective surface could be sensed as poor, if the sensor is slightly misplaced from the proper divergence angle, as the sensor could erroneously detect and record a relatively low intensity of the retroreflected light. With regard to the curve 47, if the divergence angle had an error of 0.2° a large difference could be measured in the light intensity.

Further, any sensor system should sense and record what the eye sees and perceives. The retroreflectometer described herein can utilize a small diameter pinhole over the sensor to improve the system's resolution. The ideal pinhole diameter would match the subtended angle of the human eyes' night-accommodated dilated pupil size of approximately 8 mm.

The retroreflectometer herein can, for the first time, provide to one having skill in the art or quality control person desiring to record the effects of retroreflective surfaces, the ability to measure minute changes in the optical properties of retroreflective materials. As these retroreflective materials age, the optical properties can change. For instance, in cube-corner prismatic retroreflective surfaces, prism distortions can arise. Light scattering can occur in many retroreflective products. The integral under the divergence angle curve (FIG. 3) at fixed incidence angles is a measure of the efficiency of the retroreflective material. As materials age, their properties may be evaluated on the basis of changes in the integrated value. For example, light scattering or absorption within the retroreflective material would reduce, but would not necessarily change, the sensed and recorded curve.

The retroreflectometer described herein can make retroreflective measurements faster than the prior art methods. In addition, the retroreflectometer can be used by persons having relatively little skill in the art. The retroreflectometer allows highly accurate optical retroreflective measurements even to such unskilled persons. The retroreflectometer also allows for the direct generation of the retroreflective properties of surfaces as functions of variables such as the divergence and incidence angles, via X-Y plotters which provide a quick printout of the special optical properties of the retroreflective materials being evaluated.

The retroreflectometer also permits the recording of optical properties at points other than those defined in the typical government procurement specifications. The retroreflectometer can provide an output signal which can be utilized, such as by digitizing and mathematically manipulating to plot photopic, scotopic or radiometric values. Data digitally stored can be later retrieved to evaluate and compare such data to later obtained retroreflective data. For example, optical aging characteristics can be studied.

Measurements made by the retroreflectometer herein described are generally more accurate than measurements previously made by the state-of-the-art instruments. The retroreflectometer herein more closely duplicates the observer's perception and brightness of retroreflective materials than instruments currently being used to measure such retroreflective properties. The retroreflectometer also provides for the divergence and incidence angles to be changed simultaneously to simulate the optical conditions experienced by a driver approaching an illuminated retroreflective sign at night. The retroreflectometer herein performs a task heretofore difficult or impossible to perform with state-of-the-art equipment. For example, such state-of-the-art equipment was unable to identify loss of retroreflective intensity at specific divergence angles. The retroreflectometer herein provides the ability to plot retroreflectivity versus divergence from zero through 50° incidence angles. By integration, changes in optical elements form can be identified separately from the combined effects of absorbed and scattered light.

What is claimed is:

1. Apparatus for measuring retroreflective properties of a surface, the apparatus comprising:
   (a) a light source for providing a beam of light;
   (b) support means for supporting a surface being evaluated for its retroreflective properties, positioned to enable the beam of light to strike the surface being evaluated, which support means is capable of rotating for changing the angle of incidence of the light striking the supported surface being evaluated;
   (c) a beamsplitter for reflecting the beam of light from the light source to the surface being evaluated and transmitting light retroreflected from the surface;
   (d) a lens, positioned between the beamsplitter and said surface, for collimating the beam of light reflected from the beamsplitter and focusing the light retroreflected from the surface being evaluated;
   (e) a sensor for detecting and measuring the intensity of retroreflected light positioned at a distance from the lens at or about equal to the focal distance of the lens;
   (f) means for moving the sensor across the focal point of the lens to change the angle of divergence at which the sensor detects such retroreflected light and adapted to cooperate with rotation of said support means to simultaneously change the measured angle of divergence with the angle of incidence; and
   (g) means for displaying the intensity of light detected by the sensor.

2. Apparatus as recited in claim 1 wherein the means for moving the sensor across the focal point of the lens comprises apparatus for moving the sensor horizontally across the focal point of the lens.

3. Apparatus as recited in claim 1 or 2 wherein the means for moving the sensor across the focal point of the lens comprises apparatus for moving the sensor vertically across the focal point of the lens.

4. Apparatus as recited in claim 1 further comprising an apertured surface positioned near the light source for providing a point source of light from the light source.

5. Apparatus as recited in claim 1 further comprising an apertured surface positioned in front of the sensor for controlling the amount of light striking the sensor.

6. Apparatus as recited in claim 1 further comprising a housing surrounding the apparatus for preventing outside light from entering the housing and affecting a measurement of retroreflective properties of a surface.

7. Apparatus as recited in claim 6 further comprising a reflective surface positioned between the lens and means for supporting a surface, which reflective surface reflects collimated light from the lens at about a right angle outwardly of the housing through an opening in the housing and which reflective surface reflects light entering the opening in the housing through the lens.

8. Apparatus as recited in claim 1 wherein the means for displaying the intensity of light detected by the sensor comprises display means for indicating the intensity of the light as a function of the angle of incidence of light on the surface being evaluated or as a function of the position of the sensor.

9. A method for measuring the intensity of retroreflected light as a function of the angle of incidence of light striking a surface, the method comprising the steps of:
(a) forming a directed beam of light and directing the beam of light onto a beamsplitter;
(b) reflecting at least a portion of the light with the beamsplitter through a lens;
(c) collimating the light passing through the lens;
(d) projecting the collimated light onto a surface at a measurable angle of incidence;
(e) passing light retroreflected from the surface through the lens for focusing at least a portion of the light through the beamsplitter and onto a light intensity sensor;
(f) measuring the intensity of retroreflected light striking the sensor as a function of angle of divergence while simultaneously changing the angle of incidence of collimated light onto said surface with the measured angle of divergence; and
(g) correlating the measured intensity of light striking the surface at the angle of divergence to the angle of incidence of the light striking the surface.

10. Apparatus for measuring retroreflective properties of a surface along discrete areas of the surface, the apparatus comprising:
(a) a light source for providing a beam of light;
(b) a beamsplitter spaced from the light source and positioned for reflecting the beam of light from the light source;
(c) a lens spaced from the beamsplitter and positioned to intercept the beam of light reflected from the beamsplitter, which lens collimates the reflected beam of light as it passes through the lens and which focuses light passing through the lens in the opposite direction;
(d) support means spaced from the lens for supporting a surface being evaluated for retroreflective properties, which support means is capable of traversing the collimated light from the lens;
(e) a slotted surface positioned for intercepting the collimated light before such light strikes the surface being evaluated, which slotted surface has a slot opening extending thereacross for passing a portion of the collimated light through the slotted surface as a narrow beam of collimated light which illuminates the surface being evaluated along a corresponding narrow band;
(f) a sensor spaced from the beamsplitter and positioned at a distance from the lens about equal to the focal distance of the lens for receiving retroreflected light retroreflected from the surface being evaluated and focused by the lens, which sensor detects and measures the intensity of such retroreflected light;
(g) means for moving the support means across the collimated light which includes position-monitoring means for determining the position of illumination of the sample;
(h) means for simultaneously moving the sensor and rotating the support means to simultaneously change the angle of incidence of light on the surface and the angle of divergence striking the sensor; and
(i) means for displaying the intensity of light retroreflected from the surface being evaluated at such a determined position along the surface being evaluated.

11. Apparatus as recited in claim 10 further comprising rotating means on the support means for rotating the surface being evaluated to change the angle of incidence of the collimated light illuminating the surface being evaluated.

12. Apparatus as recited in claim 11 further comprising sensor movement means for moving the sensor transversely in the focal plane of the lens.

13. Apparatus for measuring retroreflective properties of a surface, the apparatus comprising:
(a) a light source for providing a beam of light;
(b) an adjustable apertured surface positioned near the light source wherein the diameter of the aperture in the surface is adjustable for providing a point source of light;
(c) support means for supporting a surface being evaluated for its retroreflective properties such that the beam of light strikes the surface, which support means is capable of rotating for changing the angle of incidence of the light striking the surface;
(d) a beamsplitter for reflecting the beam of light from the light source to the surface being evaluated and transmitting light retroreflected from the surface;
(e) a lens positioned between the beamsplitter and surface for collimating the beam of light reflected from the beamsplitter and focusing the light retroreflected from the surface being evaluated;
(f) a sensor for detecting and measuring the intensity of retroreflected light positioned at a distance from the lens about equal to the focal distance of the lens;
(g) an adjustable apertured surface secured to the sensor wherein the diameter of the aperture in the surface is adjustable;
(h) means for moving the sensor across the focal point of the lens to change the angle of divergence at which the sensor detects such retroreflected light; and
(i) means for displaying the intensity of light detected by the sensor.

14. A method for measuring the intensity of retroreflected light as a function of both the angle of incidence of light striking a surface and the divergence angle as light is retroreflected from the surface, the method comprising the steps of:
(a) forming a directed beam of light and directing the beam of light onto a beamsplitter;
(b) reflecting at least a portion of the light with the beamsplitter through a lens;
(c) collimating the light passing through the lens;
(d) projecting the collimated light onto a surface at a measurable angle of incidence;
(e) changing the angle of incidence as the collimated light is projected on the surface;
(f) passing light retroreflected from the surface through the lens for focusing at least a portion of the light through the beamsplitter to a focal point;
(g) passing a light intensity sensor transversely through the retroreflected light at about the focal point of the lens;
(h) measuring the intensity of the retroreflected light as a function of the position of the sensor as the sensor passes through the retroreflected light;

(i) correlating the position of the sensor as it intercepts the retroreflected light with the angle of divergence of the retroreflected light; and (j) correlating the measured intensity of the retroreflected light with the determined angle of incidence and angle of divergence.

15. Apparatus for measuring retroreflective properties of a surface, the apparatus comprising:

(a) a light source for providing a beam of light;

(b) support means for supporting a surface being evaluated for retroreflective properties such that the beam of light strikes the surface, wherein such support means is rotatable for changing the angle of incidence of the light striking the surface;

(c) a beamsplitter for reflecting the beam of light from the light source to the surface being evaluated and transmitting light retroreflected from the surface;

(d) a lens positioned between the beamsplitter and the surface for collimating the beam of light reflected from the beamsplitter and focusing the light retroreflected from the surface being evaluated;

(e) a sensor for detecting and measuring the intensity of retroreflected light positioned at a distance from the lens at or about equal to the focal distance of the lens, said sensor being capable of movement to change the angle of divergence at which the sensor detects the retroreflected light;

(f) means for simultaneously moving the sensor and rotating the support means to simultaneously change the angle of incidence of light on the surface and the angle of divergence of the light from the surface detected by the sensor; and (g) means for at least displaying the intensity of light detected by the sensor.

* * * * *